(12) United States Patent
Raftery et al.

(10) Patent No.: US 8,980,637 B2
(45) Date of Patent: Mar. 17, 2015

(54) BREAST CANCER BIOMARKERS AND IDENTIFICATION METHODS USING NMR AND GAS CHROMATOGRAPHY-MASS SPECTROMETRY

(75) Inventors: Daniel M. Raftery, Lafayette, IN (US); Zhengzheng Pan, Indianapolis, IN (US); Haiwei Gu, Lauderdale, MN (US)

(73) Assignee: Purdue Research Foundation, West Lafayette, IN (US)

(*) Notice: Subject to any disclaimer, the term of this patent is extended or adjusted under 35 U.S.C. 154(b) by 230 days.

(21) Appl. No.: 12/680,655

(22) PCT Filed: Oct. 3, 2008

(86) PCT No.: PCT/US2008/078759
§ 371 (c)(1),
(2), (4) Date: Aug. 24, 2010

(87) PCT Pub. No.: WO2009/046305
PCT Pub. Date: Apr. 9, 2009

(65) Prior Publication Data
US 2010/0311600 A1 Dec. 9, 2010

Related U.S. Application Data

(60) Provisional application No. 60/977,445, filed on Oct. 4, 2007.

(51) Int. Cl.
*G01R 33/44* (2006.01)
*H01J 49/00* (2006.01)
(Continued)

(52) U.S. Cl.
CPC ............ *G01R 33/465* (2013.01); *H01J 49/004* (2013.01); *G01R 33/44* (2013.01);
(Continued)

(58) Field of Classification Search
CPC ....... G01R 33/44; G01N 24/00; G01N 24/08; G01N 24/087; G01N 24/088; G01N 2800/00; G01N 2800/0028
See application file for complete search history.

(56) References Cited

U.S. PATENT DOCUMENTS

| | | |
|---|---|---|
| 2003/0124610 A1 | 7/2003 | Kvalheim et al. |
| 2006/0027744 A1 | 2/2006 | Stults et al. |
| 2007/0221835 A1 | 9/2007 | Raferty et al. |

OTHER PUBLICATIONS

Griffin et al., "Metabolic Profiles of Cancer Cells", 2004, Nat. Rev. Cancer, 4:551-562.*

(Continued)

*Primary Examiner* — Christopher M Babic
*Assistant Examiner* — Jeremy C Flinders
(74) *Attorney, Agent, or Firm* — Bowditch & Dewey, LLP; Roger P. Zimmerman

(57) ABSTRACT

A method for the parallel identification of one or more metabolite species within a biological sample is provided. The method comprises producing a first spectrum by subjecting the sample to a nuclear magnetic resonance analysis, the first spectrum containing individual spectral peaks representative of the one or more metabolite species contained within the sample; producing a second spectrum by subjecting the sample to a mass spectrometry analysis, the spectrum containing individual spectral peaks representative of the one or more metabolite species contained within the sample; subjecting each of the individual spectral peaks to a statistical pattern recognition analysis to identify the one or more metabolite species contained within the sample; and identifying the one or more metabolite species contained within the sample by analyzing the individual spectral peaks of the mass and nuclear magnetic resonance spectra.

11 Claims, 9 Drawing Sheets

(51) Int. Cl.
*G01R 33/465* (2006.01)
*G06K 9/00* (2006.01)
*G01N 24/08* (2006.01)
*G01R 33/46* (2006.01)
*G01R 33/48* (2006.01)
*G01R 33/56* (2006.01)

(52) U.S. Cl.
CPC ... *G01R 33/4808* (2013.01); *G01N 2800/7028* (2013.01); *G01R 33/5608* (2013.01); *H01J 49/00* (2013.01); *G06K 9/00543* (2013.01); *G01N 24/08* (2013.01); *G01R 33/4625* (2013.01); *Y10S 436/813* (2013.01)
USPC .................. 436/64; 436/813; 506/6; 506/15

(56) References Cited

OTHER PUBLICATIONS

Dalluge et al., "Comprehensive Two-Dimensional Gas Chromatography: a Powerful and Versatile Analytical Tool", 2003, J. Chromatog. A, 1000:69-108.*
Trethewey et al., "Metabolite Profiling in Plants", 2007, Encyclopedia of Life Sciences, p. 1-8.*
Chajès et al., Int. J. Cancer, 1999, 83:585-590.*
Bruker 2006 webpage snapshot.*
Varian 2002 press release.*
Quevedo-Coli et al. (Biochem. Mol. Biol. Intl., 1997, 41:1-10).*
Simonsen et al. (Am. J. Clin. Nutr., 1998, 68:134-41).*
Beckwith-Hall, BM; Nicholson, JK; Nicholls, AW; Foxall, PJ; Lindon, JC; Connor, SC, Abdi, M; Connelly, J; Holmes, E; "Nuclear magnetic resonance spectroscopic and principal components analysis investigations into biochemical effects of three model hepatotoxins," Chem Res Toxicol, 1998 260-72.
Beger, RD; Schnackenbert, LK; Hollard, RD; Li, D; Dragan Y; "Metabonomic models of human pancreatic cancer using 1D proton NMR spectra of lipids in plasma," Metabolomics 2006, 2, 125-134.
Belton, PS; Colquhoun, IJ; Kemsley, EK; Delgadillo, I; Roma, P; Dennis, MJ; Sharman, M; Holmes, E; Nicholson, JK; Spraul, M; "Application of chemometrics to the 1H NMR spectra of apple juices: discrimination between apple varieties," Food Chem. 1998, 61, 207-213.
Bino, RJ; Hall, RD; Fiehn, O; Kopka, J; Saito, K; Draper, J; Nikolau, BJ; Mendes, P; Roessner [Tunali, U; Beale, MH; Trethewey, RN; Lange, BM; Wurtele, ES; Sumner, LW; "Potential of metabolomics as a functional genomics tool," Trends Plant Sci. 2004, 9, 418-425.
Brindle, JT; Antti, H; Holmes, E; Tranter, G; Nicholson, JK; Bethell, HWL; Clarke, S; Schofield, PM; McKilligen, E; Mosedale, DE; Grainger, DJ; "Rapid and noninvasive diagnosis of the presence and severity of cornary heart disease using 1H-NMR-based metabonomics," Nat Med 2002 1439-44.
Chen, H; Pan, Z; Talaty, N; Raftery, D; Cooks, RG; "Combining desorption electrospray ionization mass spectrometry and nuclear magnetic resonance for differential metabolomics without sample preparation," Rapid Comm Mass spectrom, 2006, 20, 1577-1584.
Cody, RB; Laramee, JA; Durst, HD; "Versatile New Ion Source for the Analysis of Materials in Open Air under Ambient Conditions," Anal. Chem. 2005, 77, 2297-2302.
Crockford, DJ; Holmes, E; Lindon, JC; Plumb, RS; Zirah, S; Bruce, SJ; Rainville, P.; Stumpf, CL; Nicholson, JK; "Statistical heterospectroscopy, an approach to the integrated analysis of NMR and UPLC-MS data sets: application in metabonomic toxicology studies," Anal Chem 2006 78 363-371.
El-Assaad, W; Buteau, J; Peyot, ML; Nolan, C; Roduitm R; Hardy, S; Joly, E; Dbaibo, G; Rosenbert, L; Prentki, M; "Saturated Fatty Acids Synergize with Elevated Glucose to Cause Pancreatic B-Cell Death," Endocrin. 2003, 144, 4154-4163.
Gibb, JOT; Holmes, E; Nicholson, JK; Weeks, JM; "Proton NMR spectroscopic Studies on Tissue Extracts of Invertebrate Species with Pollution Indicator Potential," Comp. Biochem. Physiol. B-Biochem. Mol. Biol. 1997, 118, 587-598.

Glunde, K; Serkova, NJ; "Therapeutic targets and biomarkers identified in cancer choline phospholipid metabolism," Pharmacogenomics 2006, 7, 1109-1123.
Gu, H; Pan, Z; Ahang, J; Raftery, D; In preparation, 2007.
Hardy, S; El-Assaad, W; Przybytkowski, E; Joly, E; Prentki, M; Langelier, Y; "Saturated Fatty Acid-induced Apoptosis in MDA-MB-231 Breast Cancer Cells," J. Biol. Chem. 2003, 278, 31861-31870.
Henson, ES; Gibson, SB; "Surviving cell death through epidermal growth factor (EGF) signal transduction pathways: implications for cancer therapy," Cell, Sig. 2006, 18, 2089-2097.
Hope, JL; Sinha, AE; Prazen, BJ; Synovec, RE; "Evaluation of the DotMap algorithm for locating analytes of interest based on mass spectral similarity in data collected using comprehensive two-dimensional gas chromatography coupled with time-of-flight mass spectrometry," J.Chrom. A 2005 1086 185-192.
Lindon, JC; Holmes, E; Nicholson, JK; Pharm. Res. 2006, 23, 1075-1088.
Lindon, JC; Holmes, E; Nicholson, JK; FEBS. 2007, 274,1140-1151.
Mohler, RE; Dombek, KM; Hoggard, JC; Young, ET; Synovec, RE; "Comprehensive two-dimensional gas chromatography time-of-flight mass spectrometry analysis of metabolites in fermenting and respiring yeast cells," Anal. chem. 2006, 78, 2700-2709.
Odunsi, K; Wollman, RM; Ambrosone, CB; Hutson, A; McCann, SE; Tammela, J; Geisler, JP; Miller, G; Sellers, T; Cliby, W; Qian, F; Keits; B; Intengan, M; Lele, S; Alderfer, JL; "Detection of epithelial ovarian cancer using 1H-NMR-based metabonomics," Int J Cancer 2005 113 782-788.
Oliver, SG; Winson, MK; Kell, DB; Baganz, F; "Systematic functional analysis of the yeast genome," Trends Bioech. 1998, 16, 373-378.
Pan, Z; Raftery, D; "Comparing and combining NMR spectroscopy and mass spectrometry in metabolomics," Anal. and Bioanal. Chem. 2007, 387, 525-527.
Pan, Z; Gu, H; Talaty, N; Chen, H; Shanaiah, N; Hainline, BE; Cooks, RG; Raftery, D; "Principal component analysis of urine metabolites detected by NMR and DESI-MS in patients with inborn errors of metabolism," Anal. Bioanal. Chem. 2007, 387, 539-549.
Pauling, L; Robinson, AB; Teranishi, R; Cary, P; "quantitative Analysis of Urine Vapor and Breath by Gas-Liquid Partition Chromatography," Proc. Nat. Acad. Sci. USA 1971, 68, 2374-2376.
Pierce, KM; Wood, LF; Wright, BW, Synovec, RE; "A comprehensive two-dimensional retention time alignment algorithm to enhance chemometric analysis of comprehensive two-dimensional separation data," Anal. Chem. 2005, 77, 7735-7743.
Pierce, KM; Hope, JL; Hoggard, JC; Synovec, RE; "A principal component analysis based method to discover chemical differences in comprehensive two-dimensional gas chromatography with time-of-flight mass spectrometry (GCxGC-TOFMS) separations of metabolites in plant samples," Talanta 2006, 70, 797-804.
Pierce, KM; Hoggard, JC; Hope, JL; Rainey, PM; Hoofnagle, AN; Jack, RM; Wright BW; Snovec, RE; "Fisher ratio method applied to third-order separation data to identify significant chemical components of metabolite extracts," Anal. Chem. 2006, 78, 5068-5075.
Remer, T; Boye, KR; Hartmann, MF; Wudy, SA; "Urinary Markers of Adrenarche: Reference Values in Healthy Subjects, Aged 3-18 Years," J. Clin. Endocr. Met. 2005, 90, 2015-2021.
Rubingh, CM; Bijlsma, S; Derks, Eppa,; Bobeldijk, I; Verheij, ER; Kochhar, S; Smilde AK; "Assessing the performance of statistical validation tools for megavariate metabolomics data," Metabolomics 2006, 2, 53-61.
Sandusky, P; Raftery, D; "Use of Selective TOCSY NMR Experiments for Quantifying Minor Components in Complex Mixtures: Application to the Metabonomics of Amino Acids in Honey," Anal. Chem. 2005, 77, 2455-2463.
Sandusky, P; Raftery, D; Anal. Chem. 2005, 7, 7717-7723.
Schulten, H; Beckey, H; Meuzelaar, HL; Boerboom, AJ; "High-resolution field ionization mass spectrometry of bacterial pyrolysis products," Anal. chem. 1973, 45, 191-195.
Shaffer, JP; "Multiple Hypothesis Testing," Ann. Rev. Psych. 1995, 46, 561-584.

(56) References Cited

OTHER PUBLICATIONS

Sinha, AE; Hope, JL; Prazen, BJ; Fraga, CG; Nilsson, EJ; Synovec, RE; "Multivariate selectivity as a metric for evaluating comprehensive two-dimensional gas chromatography-time-of-flight mass spectrometry subjected to chemometric peak deconvolution," J. Chrom. A 2004, 1056, 145-154.

Sinha, AE; Hope, JL; Prazen, BJ; Nilsson, EJ; Jack, RM; Synovec, RE; "Algorithm for locating analytes of interest based on mass spectral similarity in GCxGC-TOF-MS data: analysis of metabolites in human infant urine," J. Chrom. A 2004, 1058, 209-215.

Smilde, AK; Doornbos, DA; "Three-way methods for the calibration of chromatographic systems: Comparing PARAFAC and three-way PLS," J. Chemom. 1991, 5, 345-360.

Takats, Z; Wiseman, JM; Gologan, B; Cooks, RG; "Mass Spectrometry Sampling Under Ambient Conditions with Desorption Electrospray Ionization," Science 2004, 306, 471-473.

Trygg, J. PhD: Thesis, Umea University, 2001.

Valongo C; Cardoso, ML; Domingues, P; Almeida, L; Verhoeven, N; Salomons, G; Jakobs, C; Vilarinho, L; "Age related reference values for urine creatine and guanidinoacetic acid concentration in children and adolescents by gas chromatography-mass spectrometry," Clin Chim Acta 2004 348 155-161.

van der Greef, J; Smilde, AK; "Symbiosis of chemometrics and metabolomics: past, present, and future," J. Chemom. 2005, 19, 376-386.

Viant, MR; "Improved methods for the acquisition and interprettion of NMR metabolomic data," Biochem. Biophys. Res. comm. 2003, 310, 943-948.

von Roepenack-Lahaye, E; Degenkolb, T; Zerjeski, M; Franz, M; Roth, U; Wessjohann, L; Schmidt, J; Scheel, D; Clemens, S; "Profiling of *Arabidopsis* Secondary Metabolites by Capillary Liquid Chromatography Coupled to Electrospray Ionization Quadrupole Time-of-Flight Mass Spectrometry", Plant Physiol. 2004, 134, 548-559.

Weckwerth, W; Wenzel, K; Fiehn, O; "Process for the integrated extraction, identification and quantification of metabolites, proteins and RNA to reveal their co-regulation in biochemical networks," Proteomics 2004, 4, 78-83.

Weckwerth, Loureiro, ME; W; Wenzel, K; Fiehn, O; "Differential metabolic networks unravel the effects of silent plant phenotypes," Proc. Nat. Acad. Sci. USA 2004, 101, 7809-7814.

Xu, R; Pelicano, H; Zhou, Y; Carew; J; Feng, L; Bhalla, K; Keating, MJ; Huang, P; "Inhibition of Glycolysis in Cancer Cells: A Novel Strategy to Overcome Drug Resistance Associated with Mitochondrial Respiratory Defect and Hypoxia," Cancer Res. 205, 65, 613-621, 2005.

Zywicki, B; Catchpole, G; Draper, J; Fiehn, O; "Comparison of rapid liqud chromatography-electrospray ionization-tandem mass spectrometry methods for determination of glycoalkaloids in transgeneic field-grown potatoes," anal. Biochem. 2005, 336, 178-186.

David S. Wishart, Timothy Jewison, An Chi Guo, Michael Wilson, Craig Knox, Yifeng Liu, Yannick Djoumbou, Rupasri Mandal, Farid Aziat, Edison Dong, Souhaila Bouatra, Igor Sinelnikov, David Arndt, Jianguo Xia, Philip Liu, Faizath Yallou, Trent Bjorndahl, Rolando Perez-Pineiro, Roman Eisner, Felicity Allen, Vanessa Neveu, Russ Greiner, & Augustin Scalbert, HMDB 3.0—The Human Metabolome Database in 2013, Nucleic Acids Research, 2013, vol. 41, Database issue D801-D807.

* cited by examiner

US 8,980,637 B2

BREAST CANCER BIOMARKERS AND IDENTIFICATION METHODS USING NMR AND GAS CHROMATOGRAPHY-MASS SPECTROMETRY

RELATED APPLICATIONS

This application is a U.S. national stage application under 35 U.S.C. §371 of PCT International Patent Application Ser. No. PCT/US2008/078759, which has an international filing date of Oct. 3, 2008, designates the United States of America, and claims priority to U.S. Provisional Patent Application Ser. No. 60/977,445, filed Oct. 4, 2007. The disclosures of each of these prior applications are hereby incorporated by reference in their entirety.

STATEMENT REGARDING FEDERALLY SPONSORED RESEARCH OR DEVELOPMENT

This invention was made with government support under RR018294 awarded by National Institutes of Health. The Government has certain rights in the invention.

TECHNICAL FIELD

The present invention generally relates to small molecule biomarkers comprising a set of metabolite species useful for the early detection of breast cancer, including methods for identifying such biomarkers within biological samples by using a process that combines gas chromatography-mass spectrometry and nuclear magnetic resonance spectrometry.

BACKGROUND

Current breast cancer detection methods often involve mammographic examinations, followed by biopsy procedures. However, mammographies often produce inaccurate results and thereby force many women to undergo unnecessary biopsies, which can be both painful and expensive. To combat the problems related to poor diagnostic accuracy for a number of diseases, research efforts have recently focused on metabolomics to diagnosis diseases through the identification of various biomarkers.[1, 2] Metabolomics, which combines high resolution chemical analysis with multivariate statistics, provides a means to identify a subset of metabolites that differentiate sample populations, as well as gives detailed information regarding biochemical status changes.[3, 4] A variety of standard analytical instruments have been utilized for metabolomics applications, including Fourier transform infrared ("FTIR") spectroscopy, nuclear magnetic resonance ("NMR") spectroscopy, liquid chromatography ("LC") and gas chromatography coupled mass spectrometry ("GC-MS").[5,6-8,9,10] Moreover, several atmospheric ionization mass spectrometry ("MS") techniques have also been applied to metabolomics-based studies, including desorption electrospray ionization mass spectrometry ("DESI-MS"),[11] extractive electrospray ionization mass spectrometry ("EESI-MS") and direct analysis in real time ("DART")[12-15]

Among the analytical techniques employed in metabolomics research, NMR has been found to be a useful quantitative and reproducible tool for the analysis of biofluids. NMR has been utilized in a number of studies for detecting diseases and identifying putative biomarkers.[15-18] However, because NMR has relatively poor analytical sensitivity, it is often unable to detect species found in low concentrations within the biofluids. As such, in addition to simple 1D $^1$H-NMR, more advanced NMR approaches, such as two-dimensional ("2D") J-resolved spectroscopy and selective total correlation spectroscopy ("TOCSY") experiments, have been explored as alternative analytical techniques within the area of metabolomics research.[19-21]

Research has shown that chromatographic methods are ideal compliments to NMR-based metabolomics.[13,15,22] In particular, GC-MS has been used for metabolic profiling for over 30 years.[23, 24] GC-MS provides a sensitive and reasonably reproducible analytical platform for analysis.[25] For example, GC-MS has recently been coupled with multivariate analysis for the differentiation of extracts from Arabidopsis plants to explore the effect of silent plant genotypes.[26, 27] However, a major disadvantage of GC-MS is its limited ability to resolve and/or even detect many types of metabolites. This is problematic, particularly because complex biological samples often contain thousands of metabolites.[28] Recently, comprehensive two-dimensional GC has been coupled with time-of-flight mass spectrometry (TOF-MS) for the analysis of complex mixtures.[29-31] The advantage of two-dimensional gas chromatography ("2D GC" or "GC×GC") is its ability to add an additional and complementary second separation to the analysis. Coupled with TOF-MS, 2D GC is capable of identifying exact masses of many compounds within complex mixtures. For instance, Mohler and coworkers have used this technique to analyze metabolites in fermenting and respiring yeast.[32] Principal component analysis ("PCA") and parallel factor analysis ("PARAFAC")[33] were applied for the purposes of classification and quantification, respectively. The Synovec group has also developed different algorithms for the analysis of the multi-way data generated from GC×GC-MS including the Fisher ratio method, peak alignment, and the DotMap algorithm.[34-36]

The combination of complementary analytical techniques in metabolomics research opens a number of new opportunities.[13,15,22] The development of new and emerging technologies in metabolomics has proven to be powerful and promising in a number of cases. For NMR and MS, the combination of two essentially orthogonal analytical techniques, both having extremely high resolving power and the unequivocal ability to identify unknown metabolites, also provides a powerful approach for metabolomics research.

Data from NMR and MS experiments are generally complex since they contain qualitative/quantitative information on upwards of several hundreds of metabolites. Multivariate statistical analyses are thus used for data reduction and in particular for differentiating biofluids samples into "disease" and "control" populations based on the differences in signals of multiple metabolites. A variety of multivariate statistical methodologies provide extremely helpful tools for filtering the large amounts of data and for accessing the often-subtle biochemical perturbations latent in the spectra. In addition, these approaches can be used to extract sets of biomarker metabolites that have the best properties for the assessment of disease status. However, the use of a single analytical method to uncover useful biomarkers for early disease detection, and in particular early breast cancer detection has so far been unsuccessful.

The present invention is intended to address and/or to improve upon one or more of the problems discussed above.

SUMMARY OF THE INVENTION

The present teachings are generally related to biological sample classification methods, which utilize a combination of MS and NMR techniques. More particularly, the present teachings take advantage of the combination of NMR and two-dimensional gas chromatography-mass spectrometry ("GC×GC-MS") to identify small molecule biomarkers comprising a set of metabolite species. These identified biomarkers have been found to be useful for detecting early forms of breast cancer.

Mass and NMR spectra generated by the present methods can be analyzed with an advanced multivariate statistical pattern recognition approach, which allows sample differentiation by combining many metabolites in parallel. More particularly, the present teachings allow multiple metabolite species to be measured in parallel by using a combination of GC×GC-MS and NMR. The use of two analytical diagnostic methods provides better coverage of possible metabolites in the body, and assists with the cross-validation of the identified biomarkers.

According to one exemplary embodiment in accordance with present teachings, GC×GC-MS and NMR spectroscopy methods are combined to analyze serum samples from breast cancer patients and healthy controls. The spectral results are then evaluated using multivariate analysis tools, such as PCA (principal component analysis). Compounds showing significantly altered concentrations in breast cancer samples are identified and compared to healthy controls using an established library of exact mass (time of flight, TOF) data and then confirmed using authentic compounds. $^1$H-NMR and statistical analysis of the same samples can then be used to produce additional molecules of interest, as well as used to classify patients in classes, such as patients having "breast cancer" and patients that are "healthy." Moreover, profiles from the NMR analysis are comparable and can be combined and statistically correlated with the GC×GC-MS results. According to this exemplary method, perturbations in the glycerophospholipid metabolism can be implicated as being related to carcinogenesis.

According to another exemplary embodiment, a method for the parallel identification of one or more metabolite species within a biological sample is provided. The method comprises producing a first spectrum by subjecting the sample to a nuclear magnetic resonance analysis. The first spectrum contains individual spectral peaks that are representative of the one or more metabolite species contained within the sample. A second spectrum is also produced by subjecting the sample to a mass spectrometry analysis. The second spectrum also contains individual spectral peaks representative of the one or more metabolite species contained within the sample. Each of the individual spectral peaks is subjected to a statistical pattern recognition analysis to identify the one or more metabolite species contained within the sample. To identify the one or more metabolite species contained within the sample, the individual spectral peaks of the mass and nuclear magnetic resonance spectra are then analyzed.

In yet another exemplary embodiment, a method for the parallel identification of one or more metabolite species within a biological sample, comprises producing a first spectrum by subjecting the sample to a nuclear magnetic resonance analysis, the first spectrum containing individual spectral peaks representative of the one or more metabolite species contained within the sample; producing a second spectrum by subjecting the sample to a two-dimensional gas chromatography coupled mass spectrometry analysis, the second spectrum containing individual spectral peaks representative of the one or more metabolite species contained within the sample; performing a principle component analysis on each of the individual spectral peaks of the first and second spectra to identify the one or more metabolite species contained within the sample; and assigning the sample into a defined sample class after the one or more metabolite species within the sample are identified.

In still yet another exemplary embodiment, a method for detecting breast cancer status within a biological sample comprises measuring one or more metabolite species within the sample by subjecting the sample to a combined nuclear magnetic resonance and mass spectrometry analysis, the analysis producing a spectrum containing individual spectral peaks representative of the one or more metabolite species contained within the sample; subjecting the individual spectral peaks to a statistical pattern recognition analysis to identify the one or more metabolite species contained within the sample; correlating the measurement of the one or more metabolite species with a breast cancer status. According to this exemplary embodiment, the one or more metabolite species are selected from the group consisting of alpha-hydroxy acid, hexadecanoic acid, vaccenic acid, octadecanoic acid, lipid-CH2 signals, glycerol, lactic acid and glucose.

In yet another exemplary embodiment, a small molecule biomarker for detecting breast cancer status within a biological sample is provided. In accordance with this embodiment, the biomarker comprises one or more metabolite species selected from the group consisting of alpha-hydroxy acid, hexadecanoic acid, vaccenic acid, octadecanoic acid, lipid-CH2 signals, glycerol, lactic acid and glucose. The one or more metabolite species are measurable by a combined nuclear magnetic resonance and mass spectrometry analysis, as well as identifiable by a statistical pattern recognition analysis.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

DETAILED DESCRIPTION

Figure 1A:
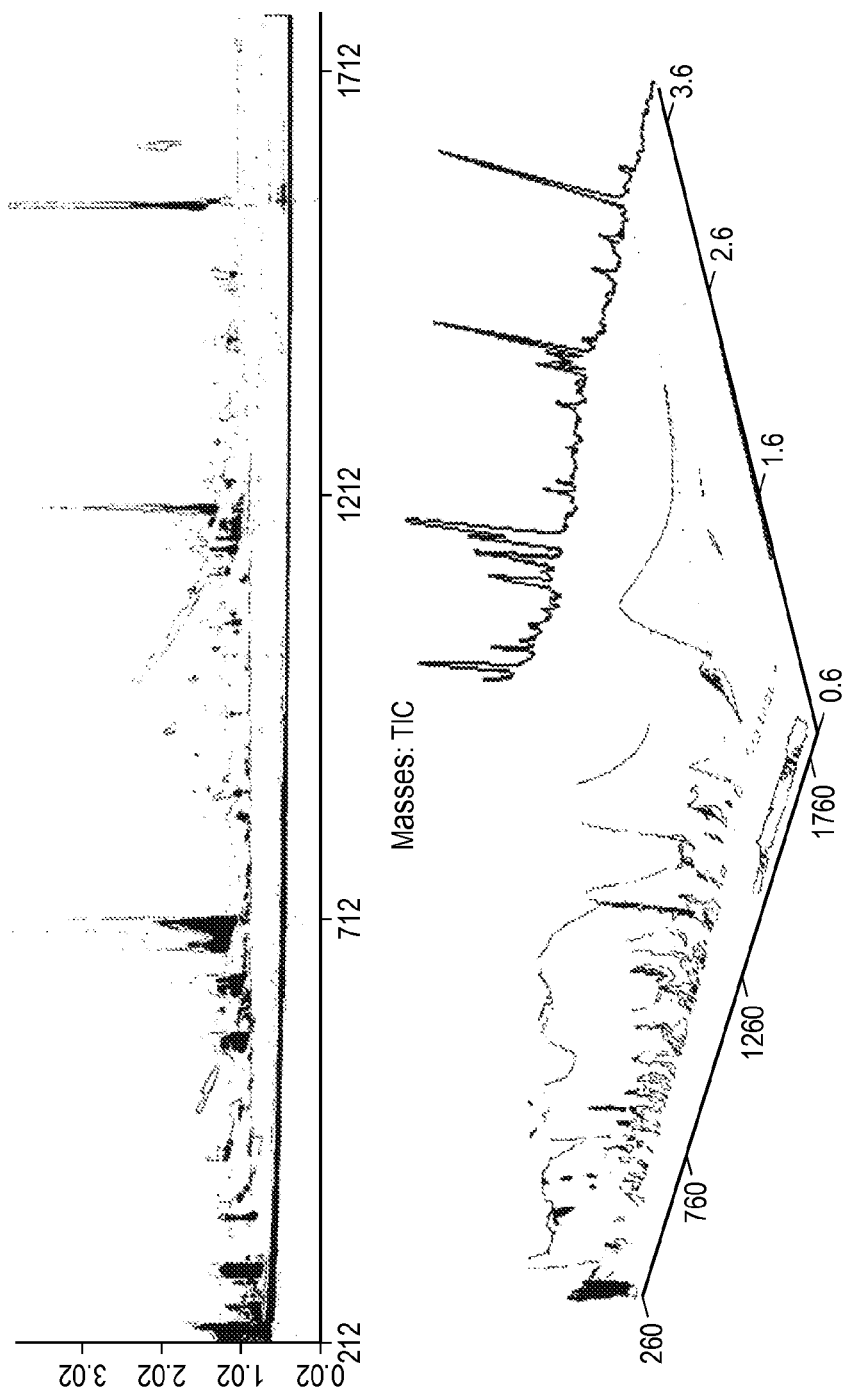
FIG. 1(a) shows GC/GC/MS spectra of serum samples from a patient having breast cancer in accordance with the present teachings.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The present teachings are generally related to the combination of GC×GC-MS and NMR for the metabolomics-based analysis of human serum samples from breast cancer patients and matched healthy controls. After GC×GC-MS and NMR measurements, a multivariate statistical method, such as PCA, is applied to reduce the data set size and complexity. While both GC×GC-MS and NMR independently have the ability to differentiate healthy and cancer patients using serum samples, the present inventors have found that combining the score plots of these two techniques results in an improved classification system. More particularly, the present method allows GC×GC-MS spectra to be statistically correlated with NMR using the statistical heterospectroscopy ("SHY") method[37], thereby allowing important metabolites that correlated with one another across the two spectroscopic methods to be identified.

Advantages and improvements of the processes and methods of the present invention are demonstrated in the following example. This example is illustrative only and is not intended to limit or preclude other embodiments of the invention.

Commercial human blood serum samples from breast cancer patients (n=20) and gender and age-matched healthy controls (n=20) were purchased from Asterand (Detroit, Mich.). All the serum samples were obtained from female volunteers of ages ranging from 40 to 75 years old. Samples were stored at −80° C. until the measurements were made.

NMR measurements were performed on a Bruker DRX 500 MHz spectrometer equipped with a room temperature HCN probe. Samples were prepared by mixing 400 µl serum with a 300 µl solution of 1.5 mM 3-(trimethylsilyl) propionic-(2,2,3,3-d4) acid sodium salt (TSP) in $D_2O$. TSP was used as the frequency standard ($\delta$=0.00). After vortexing and centrifugation, 580 µl aliquots were transferred to standard 5 mm NMR tubes for analysis. Samples were measured using a standard 1D CPMG (Carr-Purcell-Meiboom-Gill) pulse sequence coupled with water presaturation. For each spectrum, 32 transients were collected resulting in 32 k data points using a spectral width of 6000 Hz. An exponential weighting function corresponding to 0.3 Hz line broadening was applied to the free induction decay (FID) before Fourier transformation. After phasing and baseline correction using Bruker's XWINNMR software, the processed data were saved in ASCII format for further multivariate analysis. The spectral region from 4.5 to 6 ppm, which contains water and urea signals, was removed from each spectrum prior to data analysis.

For GC×GC-MS measurements, protein precipitation was first performed for each sample by mixing 200 µL serum with 200 µL methanol in a 1.5 mL Eppendorf tube. The mixture was incubated on a thermomixer at 33° C. for 15 min and then centrifuged at 15000 rpm for 5 min. The upper portion was transferred into another Eppendorf tube for future use. 200 µL chloroform was mixed with the precipitate for 1 hour at room temperature. After centrifugation, the aliquot was transferred and combined with the methanol solution from the previous step. The mixture was then lyophilized to remove the organic solvents. Each dried sample was dissolved in 100 µL pyridine, and 20 µL of this solution was mixed with 10 µL ethylhydroxylamine on a thermomixer at 60° C. for 30 min. 20 µL of the derivatization reagent MTBSTFA (N-Methyl-N-(tert-butyldimethylsilyl) trifluoroacetamide) was then added to the mixture on the same thermomixer for 60 min, resulting in the addition of a tert-butyldimethylsilyl group to active functional groups such as the hydroxyl, amino or carboxylic groups.

Derivatized samples were then transferred to the LECO Pegasus 4D GC×GC-MS instrument (St. Joseph, Mich.) for measurements. The automated LECO system facilitates a two dimensional GC capacity using a cryo-trapping unit between the two chromatographic columns. The first dimension chromatographic column was a 10 m DB-5 capillary column with an internal diameter of 180 µm and a film thickness of 0.18 µm, and the second dimension chromatographic column was a 1 m DB-17 capillary column with an internal diameter of 100 µm and a film thickness of 0.1 µm. High purity helium was used as carrier gas at a flow rate of 1.0 ml/min. The first dimension column oven ramp began at 50° C. with a hold time of 0.2 min, then increased to 300° C. at a rate of 10° C./min and held at this temperature for 5 min. The second dimension column oven began 20° C. higher than the corresponding first dimension column oven ramp with the same program rate and hold time. The second dimension separation cycle time was set for 4 seconds. 2 µL of the derivatized solutions was injected in a split mode with a ratio of 20:1. The temperatures for the inlet and transfer line were set at 280° C., and the ion source was set at 200° C. The detection and filament bias voltages were set at 1600 V and −70 V, respectively. Mass spectra ranging from 50 to 900 m/z were collected at a rate of 50 Hz, and each sample was measured twice to assure the reproducibility of the instrument. The NIST MS database (NIST MS Search 2.0, NIST/EPA/NIH Mass Spectral Library; NIST 2002) was used for data processing and peak matching.

All pre-processing and multivariate analyses of the experimental data were carried out using Matlab 7.1.0.246 (Mathworks Inc., Natick, Mass.) with the PLS toolbox (Eigenvector Research Inc, Wenatchee, Wash.). Both GC×GC-MS and NMR data were transferred from the instruments in plain text format and then imported into Matlab. Three-way GC×GC-MS data was composed of the first dimension GC retention time (in sec), the second dimension GC retention time (in sec) and corresponding TIC (total ion current). GC×GC-MS data were unfolded by inserting the second dimension data into the first dimension to form a two-column dataset. Prior to data analysis, the spectral region below 252 sec, which contains large peaks from pyridine, tert-butyldimethylsilanol and 2,2,2-trifluoro-N-methyl-acetamide, was removed. In addition, the data containing the tert-butyldimethylsilanol background peak eluting in the second GC column at about 0.6 sec was also excluded from the data analysis.

NMR spectra were binned to 1000 frequency buckets of equal width in order to remove the errors resulting from the small fluctuations of chemical shifts due to pH or ion concentration variations while the GC×GC-MS spectra were kept at full resolution. Both NMR and GC×GC-MS data were normalized against the total spectral intensity and then mean-centering was carried out prior to multivariate analysis. PCA was all performed using the PLS toolbox. For GC×GC-MS results, the corresponding loading or weight plot was folded back into the 3-way presentation format for visualization.

Figure 1B:
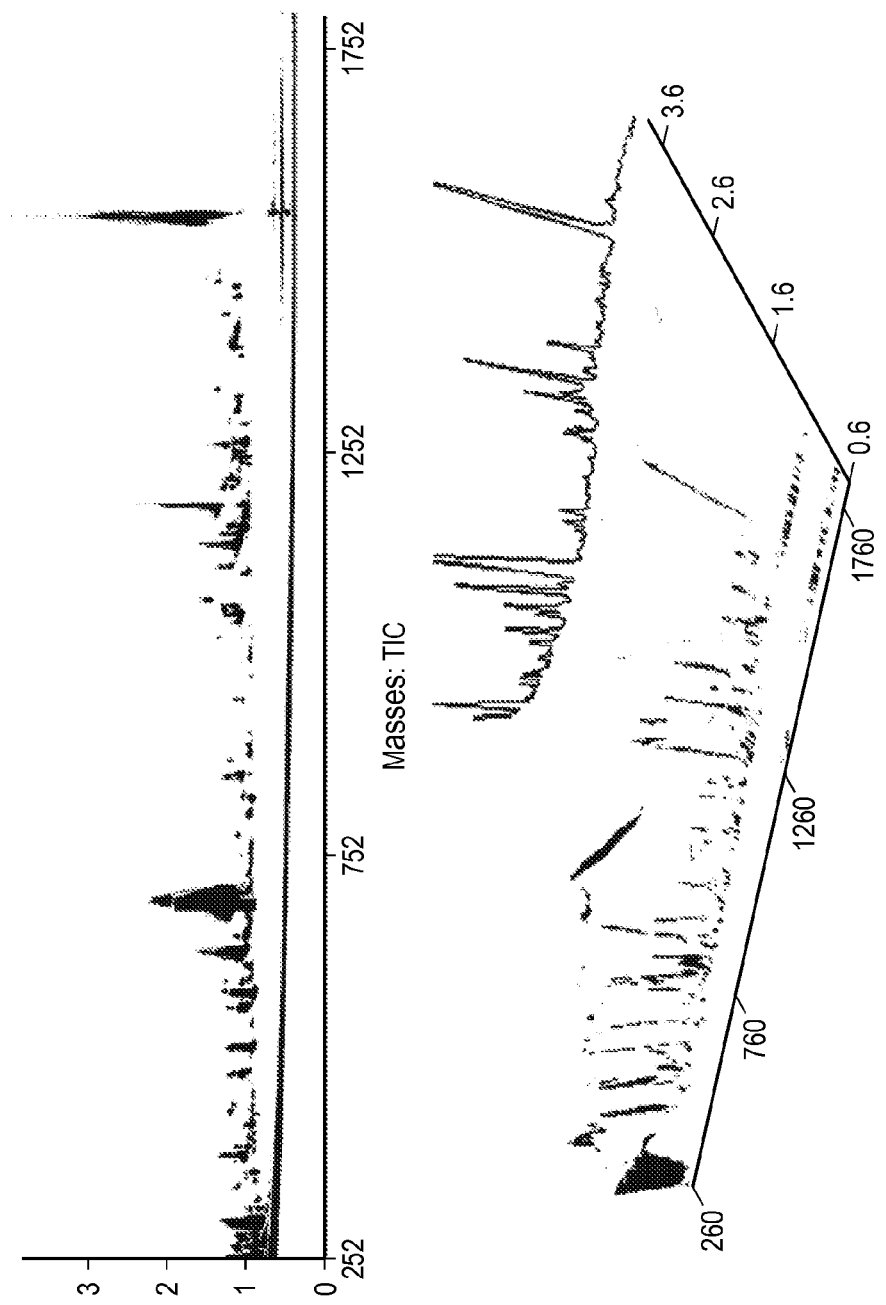
FIG. 1(b) shows GC/GC/MS spectra of serum samples from a healthy patient.

Typical GC×GC-MS spectra derived from the serum of a cancer patient and a healthy volunteer are shown in FIGS. 1a and 1b, respectively. The three-dimensional GC×GC-MS spectra are shown in the bottom of each panel, while the corresponding contour plots are shown in the upper panels. Compared with the chromatogram resulting from the first column (shown in white in the three-dimensional spectra), the unique feature of GC×GC-MS is clearly the much improved resolution due to the separation on the second GC column. More than 800 compounds could be identified in these spectra by searching against the NIST database. This complexity made it impossible to differentiate the spectra visually, and thus multivariate analysis was applied.

Figure 2:
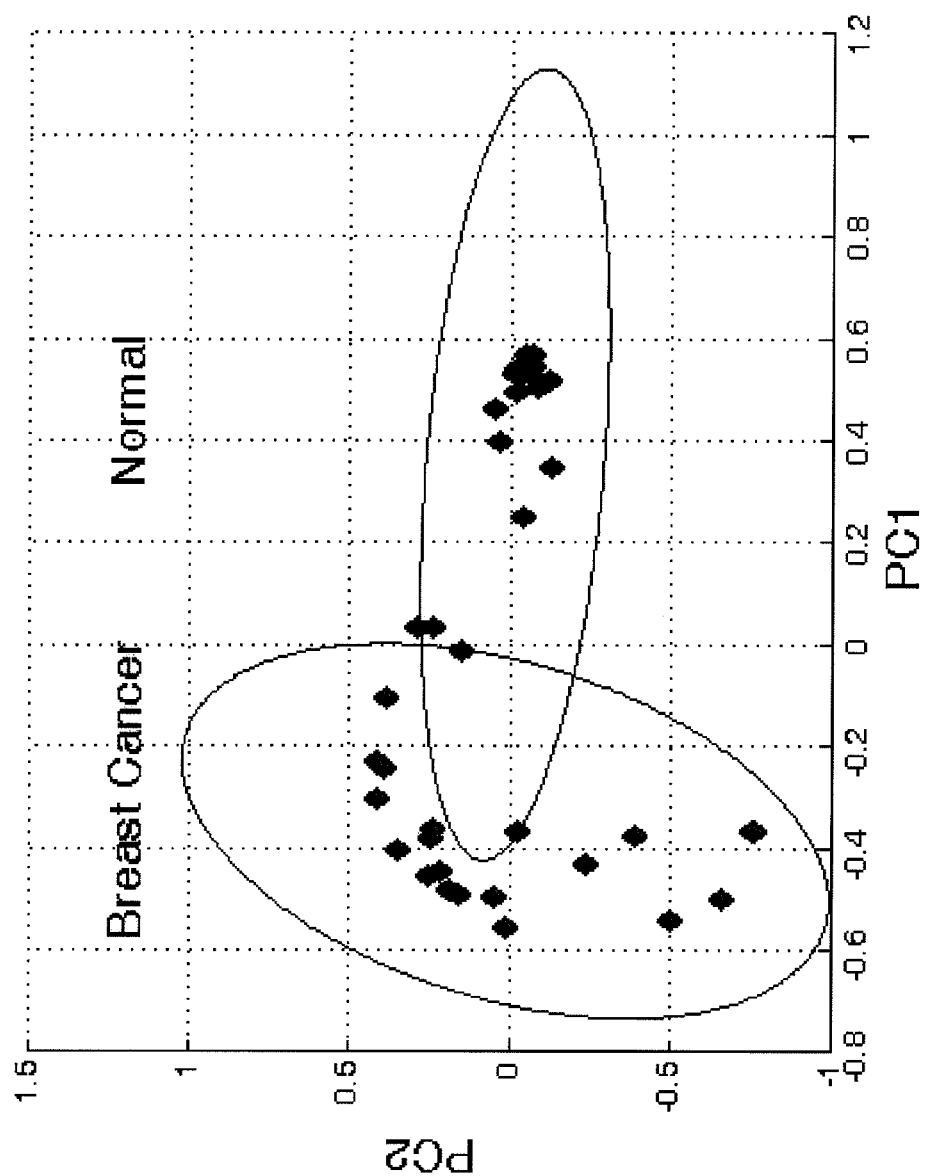
FIG. 2 shows PCA score plots from a multivariate analysis of GC/GC/MS measurements in accordance with the present teachings.

PCA was first applied to the 40 GC×GC-MS spectra. Original spectra were projected onto the two-dimensional space of the first two principal components, PC1 and PC2. The classification between breast cancer and normal samples is clearly shown in the score plot (FIG. 2), where circles indicate 95% confidence limits. Separation between the two sample groups is along PC 1 while the variation within one sample group is primarily along PC2.

Figure 3A:
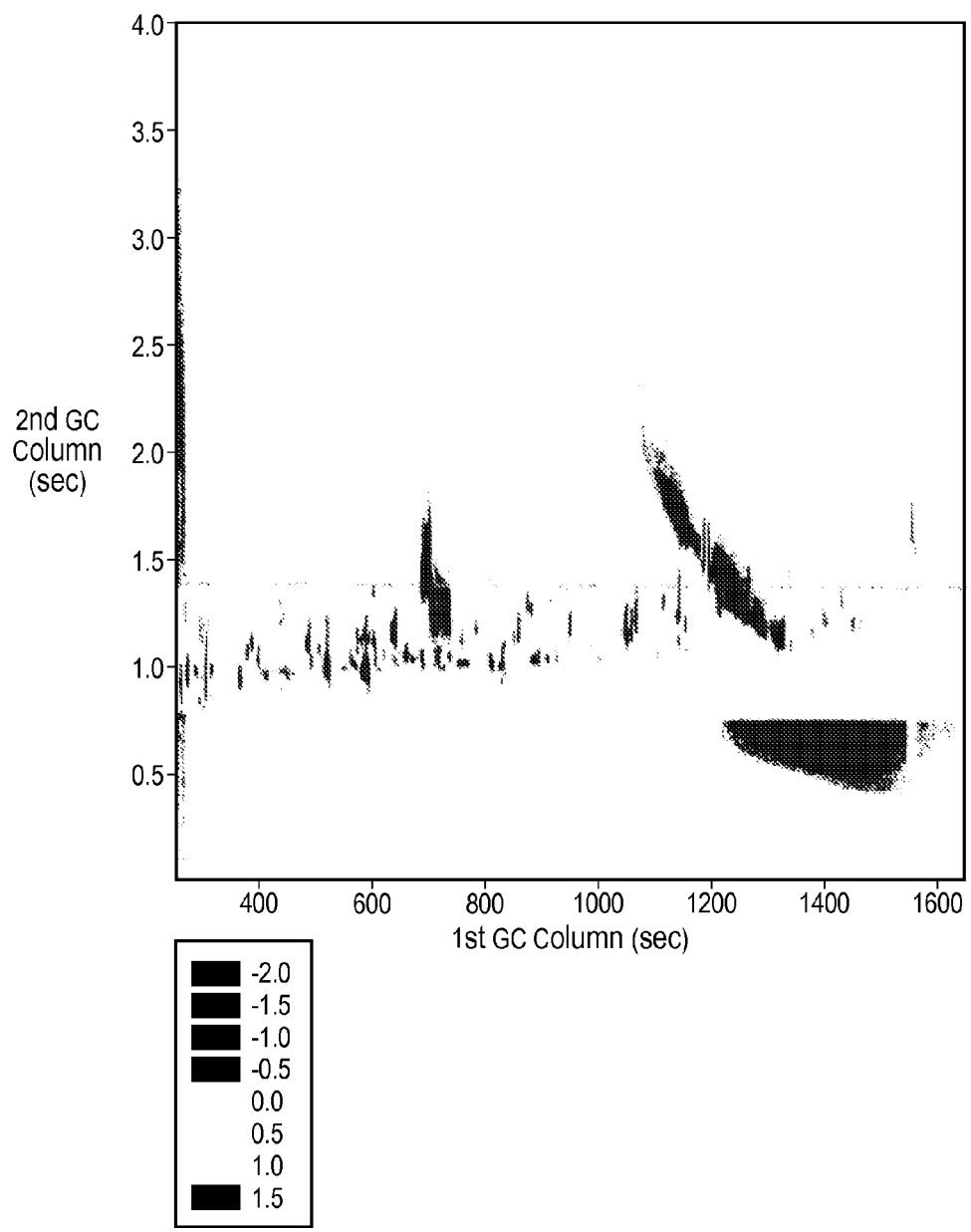
FIG. 3(a) shows a 2D representation of the PC1 loading of exemplary GC×GC-MS data in accordance with the present teachings.
Figure 3B:
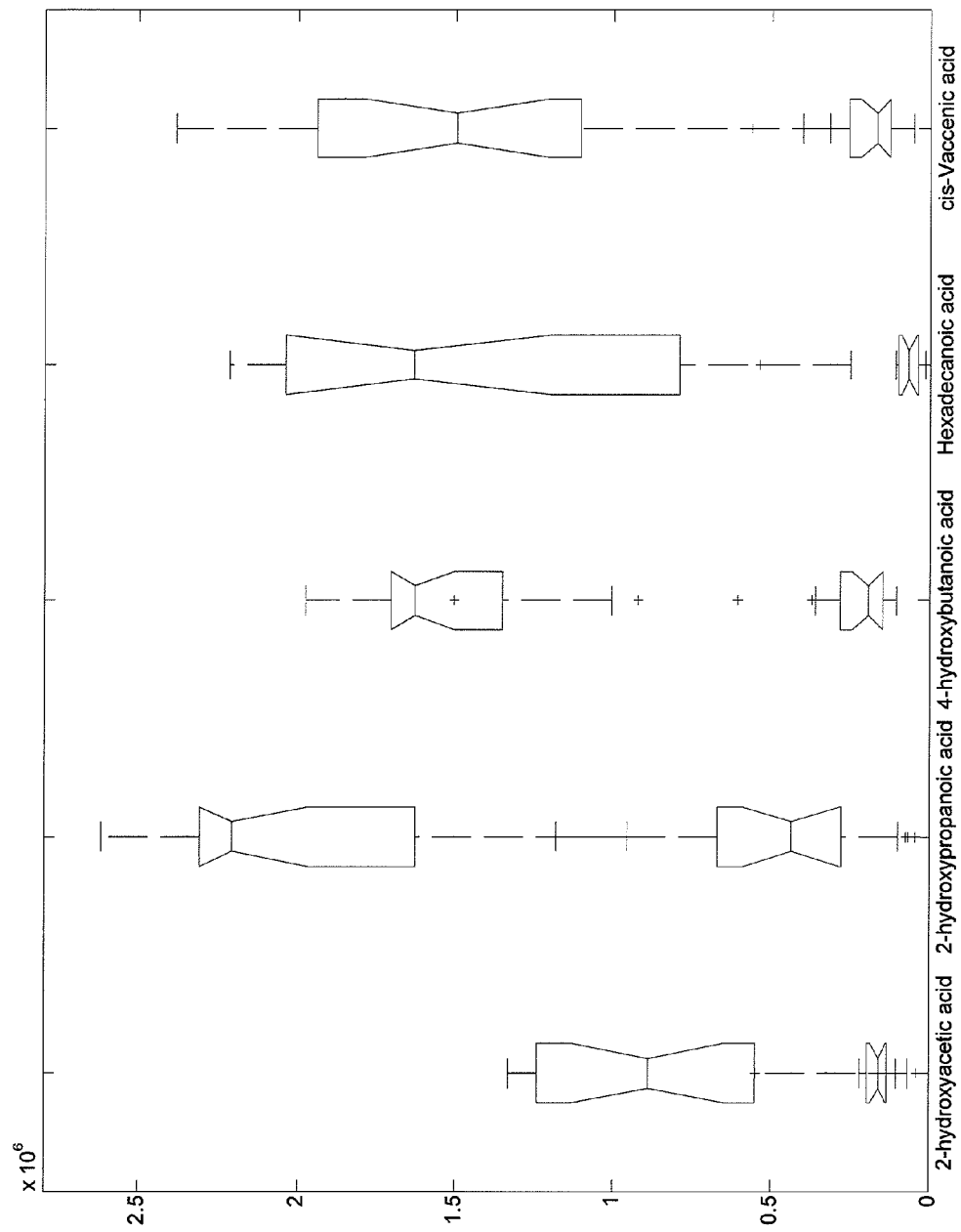
FIG. 3(b) shows a box plot of five biomarker candidates from PCA loading.

In the PCA results, breast cancer and normal samples are separated mostly along the first principal component (PC 1). The weight of PC1 is shown in FIG. 3a, in which orange and blue colors indicate up- and down-regulation, respectively, of metabolite concentrations observed in the breast cancer samples, compared to the normal samples. Identification of the seven most significant peaks was carried out by the NIST database search. Six of the compounds, which are observed to be the most altered in concentration in the cancer samples, are listed in Table 1, along with calculated p-values from the Student's t-test. These p-values are shown before any Bonferroni correction.[40] A very conservative estimate of this correction would be 1000, since approximately 800 compounds were identified in the serum samples. Five of these 6 compounds would remain significant or very close to significant ($p<0.05$) even after a Bonferroni correction of this magnitude, and the corresponding box plot indicating the altered concentrations of these five compounds is shown in FIG. 3b. The identities of the six compounds were confirmed by running GC×GC-MS experiments of authentic (commercial) compounds under the same preparation, derivatization and acquisition conditions.

TABLE 1

Compounds identified from the PCA of GC×GC-MS Data.

| Retention time (sec) | Name | Chemical structure | p-value from the Student's t-test |
|---|---|---|---|
| 637 | 2-hydroxyacetic acid | HO–C(=O)–CH$_2$OH | $8.8 \times 10^{-5}$ |
| 609 | 2-hydroxypropanoic acid | H$_3$C–CH(OH)–C(=O)OH | $5.62 \times 10^{-5}$ |
| 525 | 3-hydroxybutanoic acid | H$_3$C–CH(OH)–CH$_2$–C(=O)OH | $2.18 \times 10^{-5}$ |
| 1085 | Hexadecanoic acid | CH$_3$(CH$_2$)$_{13}$CH$_2$–C(=O)–OH | $5.48 \times 10^{-5}$ |
| 1169 | cis-Vaccenic acid | (CH$_2$)$_9$COOH / (CH$_2$)$_5$CH$_3$ | $7.71 \times 10^{-7}$ |
| 1181 | Octadecanoic acid | CH$_3$(CH$_2$)$_{15}$CH$_2$–C(=O)–OH | $5.55 \times 10^{-4}$ |

Among these compounds, a number of alpha-hydroxy acids (AHA) have been reported to be related to the development of skin cancer by affecting the expression of epidermal growth factor receptor (EGFR).[41] Fatty acids, glycerol and cholesterol are also reported to be general markers for cancer growth. Among them, hexadecanoic acid (palmitic acid), which is up-regulated in breast cancer samples, has been reported to induce cancer cell death.[42,43] More generally, it has also been reported that unsaturated acids stimulate the proliferation of human cancer cells and saturated acids inhibit it by causing apoptosis. Certainly, there are more species, which may also explain the difference between breast cancer and normal samples by comparing the library search and PCA loading; however, even using just these six compounds as a starting point for discrimination yields high classification accuracy.

In addition to the exemplary compounds listed above, it should be understood and appreciated herein that other metabolite species useful as biomarkers may also be identified in accordance with the present invention. Some of these additional metabolite species include, but are not limited to, lipid-CH2 signals (which are detectable by NMR), as well as lactic acid and glucose.

Figure 4A:
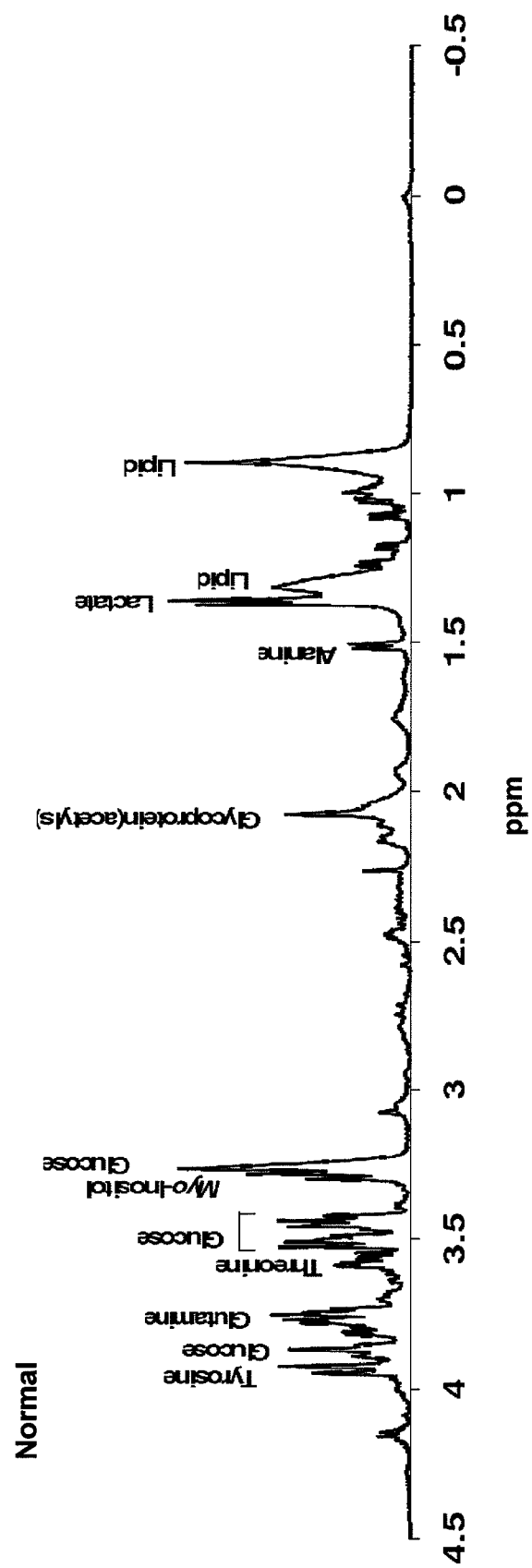
FIG. 4a shows 1D NMR spectra of a normal sample in accordance with the present teachings.
Figure 4B:
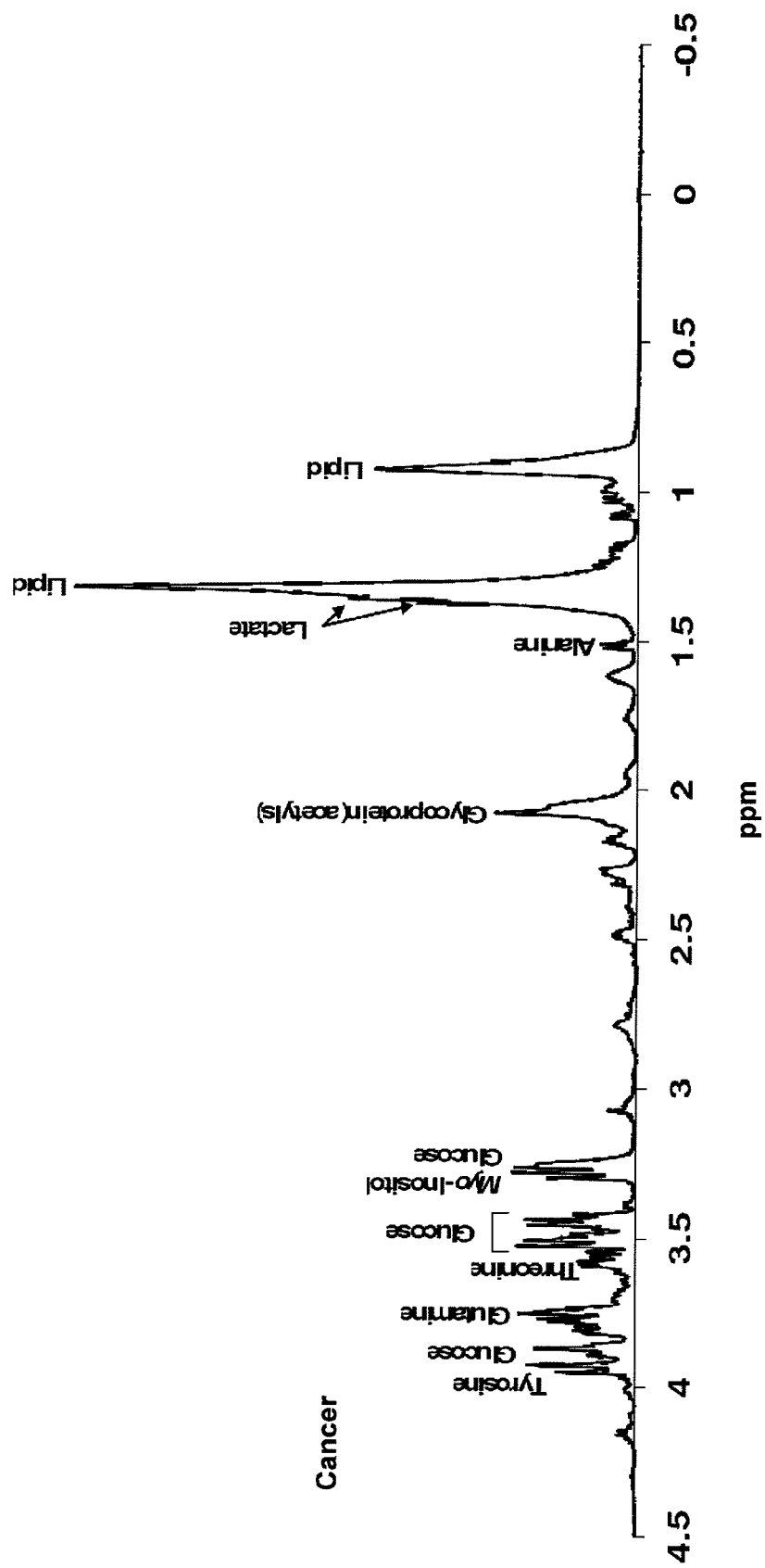
FIG. 4b shows 1D NMR spectra of a breast cancer sample in accordance with the present teachings.
Figure 5:
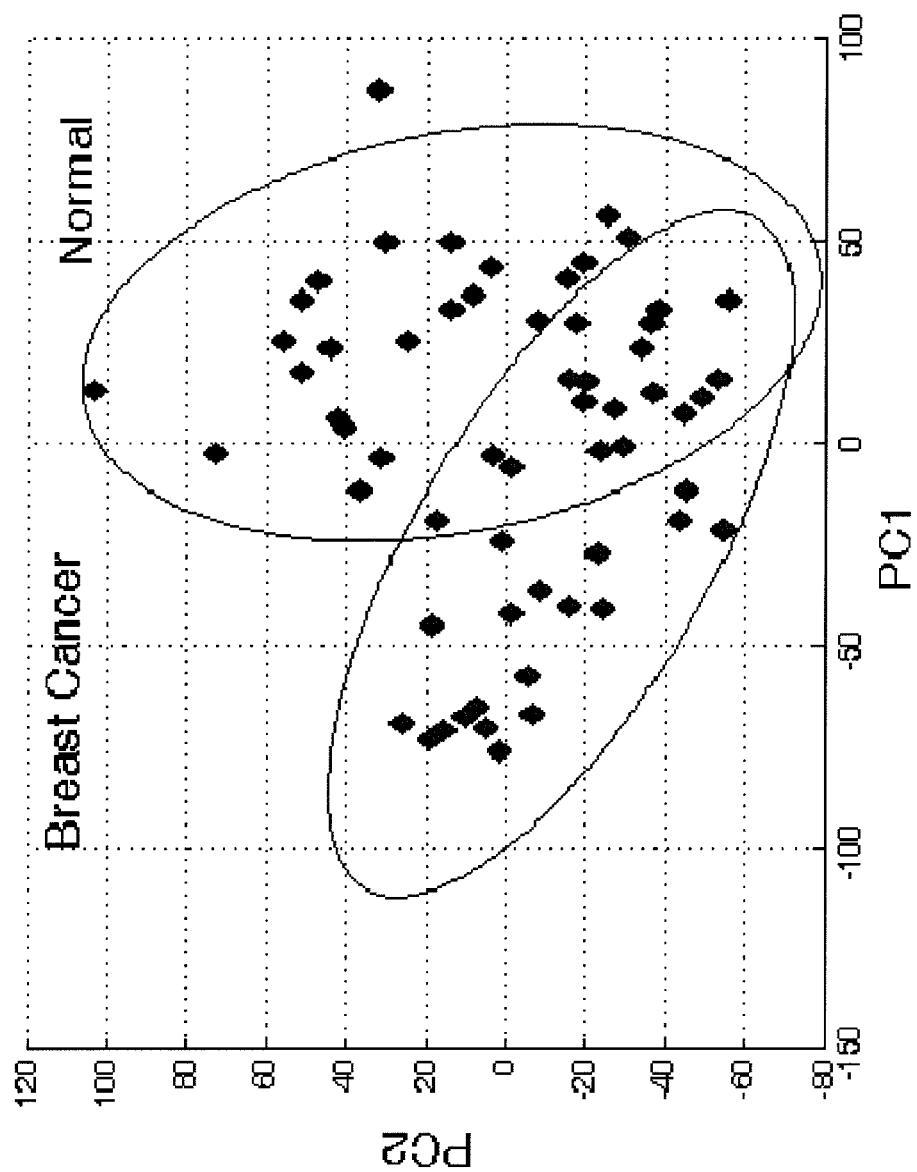
FIG. 5 shows a PCA score plot in accordance with the present teachings.
Figure 6:
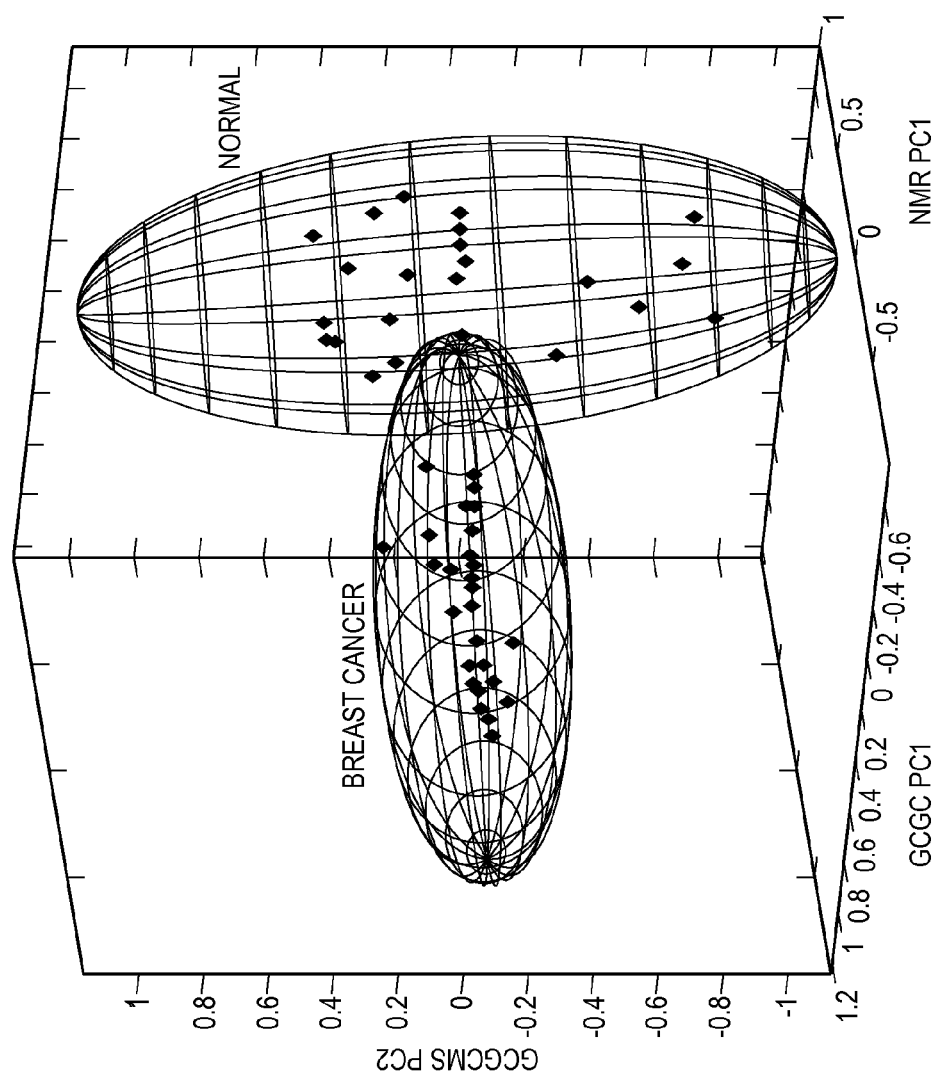
FIG. 6 shows a 3D score plot combining two PC's from NMR and one PC from GC×GC-MS in accordance with the present teachings.

NMR has been one of the major techniques in metabolomics research because of its reproducible and quantitative features. FIGS. 4a and 4b compare typical 1D CPMG spectra of breast cancer and normal samples, where only the aliphatic region is shown and compared (the intensities of the peaks in the aromatic region were very small). From visual inspection, a number of peaks appear to be clearly different between the cancer and normal samples. For example, the glucose level is decreased in the cancer sample, while the intensity of the doublet belonging to lactate at 1.34 ppm is significantly larger. Several of the broad lipid signals also have higher intensities in the NMR spectra of cancer samples. PCA was applied to the 40 NMR spectra and the score plot is shown in FIG. 5. All the samples are classified by projecting corresponding NMR spectra onto the 2D plane of PC1 and PC2 where ellipses indicate 95% confidence limits. Using a linear discrimination, a discriminant accuracy of approximately 90% was achieved. In contrast to the results of the GC×GC-MS, the separation occurs along the first two PC's, primarily along PC2, which showed 32% of the variance in the NMR data. Several putative biomarkers responsible for the separation were identified from PCA. The levels of lactate (1.33 ppm) and glucose (3.53, 3.73, 3.86 ppm) are observed to increase in breast cancer patients. In addition, lipid signals at 0.92 and 1.31 ppm are also more concentrated in the serum samples from cancer patients. The PC 1 loading is mainly contributed by the variation within the breast cancer patients, for instance, the concentration of sugars and lipids.

Previously conducted research[13] has suggested an approach to combine the PCA scores from two independent analytical techniques, DESI-MS and NMR spectroscopy, when the 2D score plot is insufficient to differentiate the samples. As shown in FIG. 5, PC1 score values from the GC×GC-MS PCA as the third dimension of the 3D score plot were used. Only a single GC×GC-MS measurement for each sample was included in the plot. The classification accuracy of NMR PCA can be improved by combining with GC×GC-MS resulting in all the samples being correctly classified. This combined approach indicates that inclusion of a second orthogonal analytical technique can be useful for improving the discrimination of similar samples.

The combination of GC×GC-MS and NMR spectroscopy, using a metabolomics approach, provides a novel and powerful approach for analyzing serum samples from breast cancer patients and healthy controls. Advanced GC×GC-MS possesses the ability to resolve and identify many more metabolites than conventional GC-MS. A good discrimination can be achieved from GC×GC-MS measurements after multivariate analysis. NMR spectroscopy also shows the capability of differentiating breast cancer from healthy control samples. More importantly, the composite PCA score plot of GC×GC-MS and NMR data improves the accuracy of classification.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

The following references are incorporated herein by reference in their entirety:
(1) Lindon, J. C.; Holmes, E.; Nicholson, J. K. *Pharm. Res.* 2006, 23, 1075-1088.
(2) Lindon, J. C.; Holmes, E.; Nicholson, J. K. *FEBS.* 2007, 274, 1140-1151.
(3) Remer, T.; Boye, K. R.; Hartmann, M. F.; Wudy, S. A. *J. Clin. Endocr. Met.* 2005, 90, 2015-2021.
(4) Valongo, C.; Cardoso, M. L.; Domingues, P.; Almeida, L.; Verhoeven, N.; Salomons, G.; Jakobs, C.; Vilarinho, L. *Clin. Chim. Acta* 2004, 348, 155-161.
(5) Oliver, S. G.; Winson, M. K.; Kell, D. B.; Baganz, F. *Trends Biotech.* 1998, 16, 373-378.
(6) Beckwith-Hall, B. M.; Nicholson, J. K.; Nicholls, A. W.; Foxall, P. J. D.; Lindon, J. C.; Connor, S. C.; Abdi, M.; Connelly, J.; Holmes, E. *Chem. Res. Toxicol.* 1998, 11, 260-272.
(7) Belton, P. S.; Colquhoun, I. J.; Kemsley, E. K.; Delgadillo, I.; Roma, P.; Dennis, M. J.; Sharman, M.; Holmes, E.; Nicholson, J. K.; Spraul, M. *Food Chem.* 1998, 61, 207-213.
(8) Gibb, J. O. T.; Holmes, E.; Nicholson, J. K.; Weeks, J. M. *Comp. Biochem. Physiol. B-Biochem. Mol. Biol.* 1997, 118, 587-598.
(9) von Roepenack-Lahaye, E.; Degenkolb, T.; Zerjeski, M.; Franz, M.; Roth, U.; Wessjohann, L.; Schmidt, J.; Scheel, D.; Clemens, S. *Plant Physiol.* 2004, 134, 548-559.
(10) Zywicki, B.; Catchpole, G.; Draper, J.; Fiehn, O. *Anal. Biochem.* 2005, 336, 178-186.
(11) Takats, Z.; Wiseman, J. M.; Gologan, B.; Cooks, R. G. *Science* 2004, 306, 471-473.
(12) Cody, R. B.; Laramee, J. A.; Durst, H. D. *Anal. Chem.* 2005, 77, 2297-2302.
(13) Chen, H. W.; Pan, Z. Z.; Talaty, N.; Raftery, D.; Cooks, R. G. *Rapid Comm. Mass Spectrom.* 2006, 20, 1577-1584.
(14) Gu, H.; Pan, Z.; Zhang, J.; Raftery, D. In preparation 2007.
(15) Pan, Z.; Gu, H.; Talaty, N.; Chen, H. W.; Hainline, B. E.; Cooks, R. G.; Raftery, D. *Anal. Bioanal. Chem.* 2007, 387, 539-549.
(16) Brindle, J. T.; Antti, H.; Holmes, E.; Tranter, G.; Nicholson, J. K.; Bethell, H. W. L.; Clarke, S.; Schofield, P. M.; McKilligin, E.; Mosedale, D. E.; Grainger, D. J. *Nature Med.* 2002, 8, 1439-1444.
(17) Beger, R. D.; Schnackenberg, L. K.; Holland, R. D.; Li, D.; Dragan, Y. *Metabolomics* 2006, 2, 125-134.
(18) Odunsi, K.; Wollman, R. M.; Ambrosone, C. B.; Hutson, A.; McCann, S. E.; Tammela, J.; Geisler, J. P.; Miller, G.; Sellers, T.; Cliby, W.; Qian, F.; Keitz, B.; Intengan, M.; Lele, S.; Alderfer, J. L. *Int. J. Cancer* 2005, 113, 782-788.
(19) Sandusky, P.; Raftery, D. *Anal. Chem.* 2005, 77, 7717-7723.
(20) Sandusky, P.; Raftery, D. *Anal. Chem.* 2005, 77, 2455-2463.
(21) Viant, M. R. *Biochem. Biophys. Res. Comm.* 2003, 310, 943-948.
(22) Pan, Z. Z.; Raftery, D. *Anal. and Bioanal. Chem.* 2007, 387, 525-527.
(23) Pauling, L.; Robinson, A. B.; Teranish.R; Cary, P. *Proc. Nat. Acad. Sci. U.S.A* 1971, 68, 2374-2376.
(24) Schulten, H. R.; Beckey, H. D.; Meuzelaa.Hl; Boerboom, A. J. *Anal. Chem.* 1973, 45, 191-195.
(25) van der Greef, J.; Smilde, A. K. *J. Chemom.* 2005, 19, 376-386.
(26) Weckwerth, W.; Loureiro, M. E.; Wenzel, K.; Fiehn, O. *Proc. Nat. Acad. Sci. U.S.A* 2004, 101, 7809-7814.
(27) Weckwerth, W.; Wenzel, K.; Fiehn, O. *Proteomics* 2004, 4, 78-83.
(28) Bino, R. J.; Hall, R. D.; Fiehn, O.; Kopka, J.; Saito, K.; Draper, J.; Nikolau, B. J.; Mendes, P.; Roessner-Tunali, U.; Beale, M. H.; Trethewey, R. N.; Lange, B. M.; Wurtele, E. S.; Sumner, L. W. *Trends Plant Sci.* 2004, 9, 418-425.
(29) Pierce, K. M.; Hope, J. L.; Hoggard, J. C.; Synovec, R. E. *Talanta* 2006, 70, 797-804.
(30) Sinha, A. E.; Hope, J. L.; Prazen, B. J.; Fraga, C. G.; Nilsson, E. J.; Synovec, R. E. *J. Chrom. A* 2004, 1056, 145-154.
(31) Sinha, A. E.; Hope, J. L.; Prazen, B. J.; Nilsson, E. J.; Jack, R. M.; Synovec, R. E. *J. Chrom. A* 2004, 1058, 209-215.
(32) Mohler, R. E.; Dombek, K. M.; Hoggard, J. C.; Young, E. T.; Synovec, R. E. *Anal. Chem.* 2006, 78, 2700-2709.
(33) Smilde, A. K.; Doornbos, D. A. *J. Chemom.* 1991, 5, 345-360.
(34) Pierce, K. M.; Hoggard, J. C.; Hope, J. L.; Rainey, P. M.; Hoofnagle, A. N.; Jack, R. M.; Wright, B. W.; Synovec, R. E. *Anal. Chem.* 2006, 78, 5068-5075.
(35) Hope, J. L.; Sinha, A. E.; Prazen, B. J.; Synovec, R. E. *J. Chrom. A* 2005, 1086, 185-192.
(36) Pierce, K. M.; Wood, L. F.; Wright, B. W.; Synovec, R. E. *Anal. Chem.* 2005, 77, 7735-7743.
(37) Crockford, D. J.; Holmes, E.; Lindon, J. C.; Plumb, R. S.; Zirah, S.; Bruce, S. J.; Rainville, P.; Stumpf, C. L.; Nicholson, J. K. *Anal. Chem.* 2006, 78, 363-371.
(38) Trygg, J. PhD Thesis, Umeå University, 2001.
(39) Rubingh, C. M.; Bijlsma, S.; Derks, E. P. P. A.; Bobeldijk, I.; Verheij, S.; Kochhar, S.; Smilde, A. K. *Metabolomics* 2006, 2, 53-61.
(40) Shaffer, J. P. *Ann. Rev. Psych.* 1995, 46, 561-584.
(41) Henson, E. S.; Gibson, S. B. *Cell. Sig.* 2006, 18, 2089-2097.
(42) El-Assaad, W.; Buteau, J.; Peyot, M. L.; Nolan, C.; Roduit, R.; Hardy, S.; Joly, E.; Dbaibo, G.; Rosenberg, L.; Prentki, M. *Endocrin.* 2003, 144, 4154-4163.
(43) Hardy, S.; El-Assaad, W.; Przybytkowski, E.; Joly, E.; Prentki, M.; Langelier, Y. *J.Biol. Chem.* 2003, 278, 31861-31870.
(44) Xu, R. H.; Pelicano, H.; Zhou, Y.; Carew, J. S.; Feng, L.; Bhalla, K. N.; Keating, M. J.; Huang, P. *Cancer Res.* 2005, 65, 613-621.

(45) Glunde, K.; Serkova, N. J. *Pharmacogenomics* 2006, 7, 1109-1123.

What is claimed is:

1. A method for the parallel identification of metabolite species within a biological sample, comprising:
   producing a first spectrum by subjecting the sample to a nuclear magnetic resonance analysis, the first spectrum containing individual spectral peaks representative of the metabolite species contained within the sample;
   producing a second spectrum by subjecting the sample to a mass spectrometry analysis, the second spectrum containing individual spectral peaks representative of the metabolite species contained within the sample;
   subjecting each of the individual spectral peaks to a statistical pattern recognition analysis to identify the metabolite species contained within the sample; and
   identifying only each of a selected subset of metabolite species consisting of 2-hydroxyacetic acid, 2-hydroxypropanoic acid, 3-hydroxybutanoic acid, hexadecanoic acid, cis-vaccenic acid and octadecanoic acid contained within the sample by analyzing the individual spectral peaks of the first and second spectra.

2. The method of claim 1, wherein the sample comprises a biofluid.

3. The method of claim 2, wherein the biofluid is blood.

4. The method of claim 1, wherein subjecting the sample to a mass spectrometry analysis comprises subjecting the sample to a two-dimensional gas chromatography coupled mass spectrometry analysis.

5. The method of claim 1, wherein subjecting each of the individual spectral peaks to a statistical pattern recognition analysis comprises subjecting the spectral peaks to a principle component analysis.

6. The method of claim 1, further comprising comparing the metabolite species to data controls contained within an exact mass (time of flight) library.

7. The method of claim 5, further comprising assigning the sample into a defined sample class of either normal control or breast cancer patient.

8. A method for the parallel identification of metabolite species within a biological sample, comprising:
   producing a first spectrum by subjecting the sample to a nuclear magnetic resonance analysis, the first spectrum containing individual spectral peaks representative of the metabolite species contained within the sample;
   producing a second spectrum by subjecting the sample to a two-dimensional gas chromatography coupled mass spectrometry analysis, the second spectrum containing individual spectral peaks representative of the metabolite species contained within the sample;
   performing a principle component analysis on each of the individual spectral peaks of the first and second spectra to identify only each of a selected subset of metabolite species consisting of 2-hydroxyacetic acid, 2-hydroxypropanoic acid, 3-hydroxybutanoic acid, hexadecanoic acid, cis-vaccenic acid and octadecanoic acid contained within the sample by analyzing the individual spectral peaks of the first and second spectra, and
   assigning the sample into a defined sample class after each of the selected subset of metabolite species within the sample are identified.

9. The method of claim 8, wherein the sample comprises a biofluid.

10. The method of claim 9, wherein the biofluid is blood.

11. The method of claim 8, further comprising comparing the metabolite species to data controls contained within an exact mass (time of flight) library.

* * * * *